(12) United States Patent
Huang (10) Patent No.: US 9,029,142 B2
(45) Date of Patent: May 12, 2015

(54) RECOMBINANT VECTORS AND HOSTS COMPRISING HUMAN GLUCOKINASE ENCODING GENE

(76) Inventor: Haidong Huang, Beijing (CN)

(\*) Notice: Subject to any disclaimer, the term of this patent is extended or adjusted under 35 U.S.C. 154(b) by 0 days.

(21) Appl. No.: 13/178,058

(22) Filed: Jul. 7, 2011

(65) Prior Publication Data

US 2011/0286984 A1    Nov. 24, 2011

Related U.S. Application Data

(63) Continuation of application No. PCT/CN2010/070038, filed on Jan. 6, 2010.

(30) Foreign Application Priority Data

Jan. 7, 2009 (CN) .......................... 2009 1 0000087

(51) Int. Cl.
| | |
|---|---|
| C12N 1/21 | (2006.01) |
| C12N 5/10 | (2006.01) |
| C12N 15/12 | (2006.01) |
| C12N 15/52 | (2006.01) |
| C12N 15/54 | (2006.01) |
| C12N 15/70 | (2006.01) |
| C12N 15/85 | (2006.01) |
| A61K 38/45 | (2006.01) |
| A61K 48/00 | (2006.01) |
| C12N 15/86 | (2006.01) |
| A61K 31/711 | (2006.01) |
| A61K 31/713 | (2006.01) |
| A61K 31/7088 | (2006.01) |
| A61P 3/08 | (2006.01) |
| A61P 3/10 | (2006.01) |
| C12N 7/01 | (2006.01) |
| C12N 9/12 | (2006.01) |
| C12N 15/03 | (2006.01) |
| C12N 15/07 | (2006.01) |
| C12N 15/63 | (2006.01) |
| C12N 15/90 | (2006.01) |

(52) U.S. Cl.
CPC ....... *A61K 31/713* (2013.01); *A01K 2267/0362* (2013.01); *A61K 38/45* (2013.01); *A61K 48/005* (2013.01); *C12N 9/1205* (2013.01); *C12N 15/86* (2013.01); *C12N 2710/10343* (2013.01); *C12Y 207/01002* (2013.01)

(58) Field of Classification Search
None
See application file for complete search history.

(56) References Cited

U.S. PATENT DOCUMENTS

| | | | |
|---|---|---|---|
| 6,689,600 B1 * | 2/2004 | Wu et al. .................... | 435/235.1 |
| 2003/0055017 A1 * | 3/2003 | Schwartz et al. ............... | 514/44 |
| 2007/0020237 A1 * | 1/2007 | Yoon et al. ................... | 424/93.2 |
| 2007/0219346 A1 | 9/2007 | Trifiro | |

FOREIGN PATENT DOCUMENTS

| | | | |
|---|---|---|---|
| WO | 0249423 A1 | | 6/2002 |
| WO | 2005/051320 A2 | | 6/2005 |
| WO | PCT/US2004/0039550 | * | 6/2005 |
| WO | 2006/043036 A2 | | 4/2006 |
| WO | WO 2009021276 A1 | * | 2/2009 |
| WO | 2010078842 A1 | | 7/2010 |

OTHER PUBLICATIONS

Zelphati et al., Stable and monodisperse lipoplex formulations for gene delivery, Gene Ther. 5(9):1272-82, 1998.*
Hank, Hank's balanced salt solution and pH control, Tissue Culture Association Manual, 1975, 1, 3-4.*
Hanks' Balance Salt Solution (1X), Gibco Catalog No. 14025 (Lot No. 3069645), 2002, www.invitrogen.com/gibco.*
Bain et al., An adenovirus vector for efficient RNA interference-mediated suppression of target genes insulinoma cells and pancreatic islets of Langerhans, Diabetes, 2004, 53, 2190-94.*
Poy et al., A pancreatic islet-specific microRNA regulates insulin secretion, Nature, 2004, 432, 226-30.*
Shantikumar et al., Role of microRNAs in diabetes and its cardiovascular complications, Cardiovascular Res., 2012, 93, 583-93.*
Canadian Office Action cited in Canadian Application No. 2,749,180 dated Jan. 15, 2013, 3 pgs.
Korean Office Action cited in Korean Application No. 10-2011-7017931 dated Nov. 8, 2012, 4 pgs.
EP Search Report cited in EP Application No. 10729101.5 dated Oct. 25, 2012, 10 pgs.
First New Zealand Office Action cited in New Zealand Application No. 593893 dated Aug. 17, 2011, 2 pgs.
Second New Zealand Office Action cited in New Zealand Application No. 593893 dated Jun. 21, 2012, 1 pg.
"Biochemical Basis of Glucokinase Activation and the Regulation by Glucokinase Regulatory Protein in Naturally Occurring Mutations", Vladi V. Heredia, Thomas J. Carlson, Erin Garcia and Shaoxian Sun, Dec. 29, 2006, Journal of Biological Chemistry, vol. 281, No. 52, 8 pgs.

(Continued)

*Primary Examiner* — Robert Mondesi
*Assistant Examiner* — Todd M Epstein
(74) *Attorney, Agent, or Firm* — Cooper Legal Group LLC (57) ABSTRACT

Gene encoding human glucokinase mutant is provided. The gene has the nucleotide sequence chosen from the nucleotide sequence listed as SEQ ID NO:2 and the nucleotide sequence wherein the ORF region encodes the same amino acid sequence as the one encoded by ORF region (position 487 to 1884) of SEQ ID NO:2 and the rest of the region is same as the non-ORF region of SEQ ID NO:2. Human glucokinase mutant encoded by the gene, the recombinant vectors carrying the gene, the hosts comprising the vectors, pharmaceutical compositions thereof, uses thereof, and methods for treating and preventing diseases by using the same are provided. The human glucokinase mutant encoded by the gene has higher activity than that of the wild type human glucokinase, and thus provides a new way of controlling blood glucose and/or preventing and/or treating disturbance of carbohydrate metabolism, especially preventing and treating diabetes.

6 Claims, 4 Drawing Sheets

(56) References Cited

OTHER PUBLICATIONS

"Adenovirus-Mediated Expression of Glucokinase in the Liver as an Adjuvant Treatment for Type 8 Diabetes", Nuria Morral, Robert McEvoy, Henghang Dong, Marcia Meseck, Jennifer Altomonte, Swan Thung and Savio L.C. Woo, Human Gene Therapy 13:1561-1570, Sep. 1, 2001, 10 pgs.

"Glucokinase (GCK) Mutations in Hyper- and Hypoglycemiz: Maturity-Onset Diabetes of the Young, Permanent Neonatal Diabetes, and Hyperinsulinemia of Infancy", Anna L. Gloyn, May 15, 2003, published online in Wiley InterScience, 10 pgs.

"Phenogypic Correction of Diabetic Mice by Adenovirus-Mediated Glucokinase Expression", Urvi J. Desai, Eric D. Slosberg, Brian R. Boettcher, Shari L. Caplan Barbara Fanelli, Zouhair Stephan, Vicky J. Gunther, Michael Kaleko and Sheila Connelly, Oct. 2001, Diabetes, vol. 50, 10 pgs.

Perspectives in Diabetes, "The Network of Glucokinase-Expressing Cells in Glucose Homeostasis and the Potential of Glucokinase Activators for Diabetes Therapy", Franz M. Matschinsky, Mark A. Magnuson, Dorothy Zelent, Tom L. Jetton, Micolai Dollba, Yi Han, Rebecca Taub and Joseph Grimsby, Jan. 2006, American Diabetes Association, vol. 55, 12 pgs.

"*Homo sapiens* Glucokinase (Hexokinase 4) (GCK), Transcript Variant 1, mRNA", Webster et al. Dec. 2008, Diabetologia 52, reprinted from the Internet at: http://liucheng.name/entrez/entrez.php?acc=NM_000162&format=gb, 6 pgs.

Australian Office Action cited in Australian Application No. 2010204379 dated May 13, 2013, 3 pgs.

Reply Australian Office Action cited in Australian Application No. 2010204379 dated Jan. 21, 2014, 25 pgs.

Canadian Office Action cited in Canadian Application No. 2,749,180 dated Feb. 14, 2014, 3 pgs.

Japanese Office Action cited in Japanese Application No. 2011-544778 dated Aug. 13, 2013, 4 pgs.

Eurasian Office Action cited in Eurasian Application No. 201170917128 dated Dec. 25, 2013, 2 pgs.

Indonesian Office Action cited in Indonesian Application No. WP0201102450 dated Mar. 1, 2013, 3 pgs.

Mexican Office Action cited in Mexican Application No. MX/A/2011/007263 dated Jul. 17, 2013, 3 pgs.

ARIPO Office Action cited in ARIPO Application No. AP/P/2011/005814 dated Aug. 6, 2014, 8 pgs.

EP Office Action cited in EP Application No. 10729101.5 dated Mar. 26, 2014. 7 pgs.

Eurasian Office Action cited in Eurasian Application No. 201170917128 dated Oct. 1, 2014, 4 pgs.

Indian Office Action cited in Indian Application No. 1503/MUMNP/2011 dated Sep. 30, 2014, 2 pgs.

African Office Action cited in African Application No. AP/P/2011/005814 dated Jun. 1, 2010, 8 pgs.

EP Communication cited in EP Application No. 10729101.5 dated May 26, 2014, 7 pgs.

Japanese Office Action cited in Japanese Application No. 2011-544778 dated Jun. 23, 2014, 3 pgs.

Philippine Office Action cited in Philippine Application No. 1/2011/501380 dated May 26, 2014, 2 pgs.

Thailand Office Action cited in Thailand Application No. 1101011042 dated Nov. 4, 2013, 1 pg.

Israeli Office Action cited in Israeli Application No. 213750 dated Aug. 10, 2014, 1 pg.

* cited by examiner

```
                        SEQUENCE LISTING

<160> NUMBER OF SEQ ID NOS: 2

<210> SEQ ID NO 1
<211> LENGTH: 2749
<212> TYPE: DNA
<213> ORGANISM: Homo sapiens

<400> SEQUENCE: 1
actccacacc tggctggagc aggaaatgcc gagcggcgcc tgagccccag ggaagcaggc      60
taggatgtga gagacacagt cacctgcagc ctaattactc aaaagctgtc cccaggtcac     120
agaagggaga ggacatttcc cactgaatct gtctgaagga cactaagccc cacagctcaa     180
cacaaccagg agagaaagcg ctgaggacgc cacccaagcg cccagcaatg gccctgcctg     240
gagaacatcc aggctcagtg aggaagggtc cagaagggaa tgcttgccga ctcgttggag     300
```

```
aacaatgaaa aggaggaaac tgtgactgaa cctcaaaccc caaaccagcc cgaggagaac    360
cacattctcc cagggaccca gggcgggccg tgacccctgc ggcggagaag ccttggatat    420
ttccacttca gaagcctact ggggaaggct gaggggtccc agctcccccac gctggctgct    480 gtgcagatgc tggacgacag agccaggatg gaggccgcca agaaggagaa ggtagagcag    540
atcctggcag agttccagct gcaggaggag gacctgaaga aggtgatgag acggatgcag    600
aaggagatgg accgcggcct gaggctggag acccatgaag aggccagtgt gaagatgctg    660
cccacctacg tgcgctccac cccagaaggc tcagaagtcg gggacttcct ctccctggac    720
ctgggtggca ctaacttcag ggtgatgctg gtgaaggtgg agaaggtga ggaggggcag     780 tggagcgtga agaccaaaca ccagatgtac tccatccccg aggacgccat gaccggcact    840
gctgagatgc tcttcgacta catctctgag tgcatctccg acttcctgga caagcatcag    900
atgaaacaca agaagctgcc cctgggcttc accttctcct ttcctgtgag gcacgaagac    960
atcgataagg gcatccttct caactggacc aagggcttca aggcctcagg agcagaaggg   1020
aacaatgtcg tggggcttct gcgagacgct atcaaacgga gaggggactt tgaaatggat   1080
gtggtggcaa tggtgaatga cacggtggcc acgatgatct cctgctacta cgaagaccat   1140
cagtgcgagg tcggcatgat cgtgggcacg ggctgcaatg cctgctacat ggaggagatg   1200
cagaatgtgg agctggtgga gggggacgag ggccgcatgt gcgtcaatac cgagtggggc   1260
gccttcgggg actccggcga gctggacgag ttcctgctgg agtatgaccg cctggtggac   1320
gagagctctg caaaccccgg tcagcagctg tatgagaagc tcataggtgg caagtacatg   1380
ggcgagctgg tgcggcttgt gctgctcagg ctcgtggacg aaaacctgct cttccacggg   1440
gaggcctccg agcagctgcg cacacgcgga gccttcgaga cgcgcttcgt gtcgcaggtg   1500
gagagcgaca cgggcgaccg caagcagatc tacaacatcc tgagcacgct ggggctgcga   1560
ccctcgacca ccgactgcga catcgtgcgc cgcgcctgcg agagcgtgtc tacgcgcgct   1620
gcgcacatgt gctcggcggg gctggcgggc gtcatcaacc gcatgcgcga gagccgcagc   1680
gaggacgtaa tgcgcatcac tgtgggcgtg gatggctccg tgtacaagct gcaccccagc   1740
ttcaaggagc ggttccatgc cagcgtgcgc aggctgacgc ccagctgcga gatcaccttc   1800
atcgagtcgg aggagggcag tggccggggc gcggccctgg tctcggcggt ggcctgtaag   1860
aaggcctgta tgctgggcca gtgagagcag tggccgcaag cgcagggagg atgccacagc   1920
cccacagcac ccaggctcca tggggaagtg ctccccacac gtgctcgcag cctggcgggg   1980
caggaggcct ggccttgtca ggacccaggc cgcctgccat accgctgggg aacagagcgg   2040
gcctcttccc tcagttttc ggtgggacag ccccagggcc ctaacggggg tgcggcagga    2100
gcaggaacag agactctgga agccccccac ctttctcgct ggaatcaatt tcccagaagg   2160
gagttgctca ctcaggactt tgatgcattt ccacactgtc agagctgttg gcctcgcctg   2220
ggcccaggct ctgggaaggg gtgccctctg atcctgctg tggcctcact tccctgggaa    2280
ctcatcctgt gtggggaggc agctccaaca gcttgaccag acctagacct gggccaaaag   2340
ggcagccagg ggctgctcat cacccagtcc tggccatttt cttgcctgag gctcaagagg   2400
cccagggagc aatgggaggg ggctccatgg aggaggtgtc ccaagctttg aatacccca    2460 gagaccttt ctctcccata ccatcactga gtggcttgtg attctgggat ggaccctcgc    2520
agcaggtgca agacagagag cccccaagcc tctgccccaa ggggcccaca aagggagaa    2580 gggccagccc tacatcttca gctccctag cgctggctca ggaagaaacc ccaagcagca    2640
ttcagcacac cccaagggac aaccccatca tatgacatgc caccctctcc atgcccaacc   2700
```
taagattgtg tgggttttt aattaaaaat gttaaaagtt ttaaacatg    2749

<210> SEQ ID NO 2
<211> LENGTH: 2748
<212> TYPE: DNA
<213> ORGANISM: Artificial Sequence
<220> FEATURE:
<223> OTHER INFORMATION: Synthetic gene encoding human glucokinase
      mutant

<400> SEQUENCE: 2

```
actccacacc tggctggagc aggaaatgcc gagcggcgcc tgagccccag ggaagcaggc      60
taggatgtga gagacacagt cacctgcagc ctaattactc aaaagctgtc cccaggtcac     120
agaagggaga ggacatttcc cactgaatct gtctgaagga cactaagccc acagctcaa     180
cacaaccagg agagaaagcg ctgaggacgc acccaagcg cccagcaatg ccctgcctg      240
gagaacatcc aggctcagtg aggaagggtc cagaagggaa tgcttgccga ctcgttggag     300
aacaatgaaa aggaggaaac tgtgactgaa cctcaaaccc caaaccagcc cgaggagaac     360
cacattctcc cagggaccca gggcgggccg tgacccctgc ggcggagaag ccttggatat     420
ttccacttca gaagcctact ggggaaggct gaggggtccc agctcccac gctggctgct     480
gtgcagatgc tggacgacag agccaggatg gaggccgcca agaaggagaa ggtagagcag     540
atcctggcag agttccagct gcaggaggag gacctgaaga aggtgatgag acggatgcag     600
aaggagatgg accgcggcct gaggctggag acccatgaag aggccagtgt gaagatgctg     660
cccacctacg tgcgctccac cccagaaggc tcagaagtcg ggacttcct ctccctggac     720
ctgggtggca ctaacttcag ggtgatgctg gtgaaggtgg agaaggtga ggaggggcag     780
tggagcgtga agaccaaaca ccagatgtac tccatccccg aggacgccat gaccggcact     840
gctgagatgc tcttcgacta catctctgag tgcatctccg acttcctgga caagcatcag     900
atgaaacaca gaagctgccc ctgggcttc accttctcct ttcctgtgag cacgaagac      960
atcgataagg gcatccttct caactggacc aagggcttca aggcctcagg agcagaaggg    1020
aacaatgtcg tggggcttct gcgagacgct atcaaacgga gagggactt tgaaatggat    1080
gtggtggcaa tggtgaatga cacggtggcc acgatgatct cctgctacta cgaagaccat    1140
cagtgcgagg tcggcatgat cgtgggcacg ggctgcaatg cctgctacat ggaggagatg    1200
cagaatgtgg agctggtgga gggggacgag ggccgcatgt gcgtcaatac cgagtggggc    1260
gccttcgggg actccggcga gctggacgag ttcctgctgg agtatgaccg cctggtggac    1320
gagagctctg caaaccccgg tcagcagctg tatgagaagc tcataggtgg caagtacatg    1380
ggcgagctgg tgcggcttgt gctgctcagg ctcgtggacg aaaacctgct cttccacggg    1440
gaggcctccg agcagctgcg cacacgcgga gccttcgaga cgcgcttcgt gtcgcaggtg    1500
gagagcgaca cggcgaccg caagcagatc tacaacatcc tgagcacgct ggggctgcga    1560
ccctcgacca ccgactgcga catcgtgcgc cgcgcctgcg agagcgtgtc tacgcgcgct    1620
gcgcacatgt gctcggcggg gctggcgggc gtcatcaacc gcatgcgcga gagccgcagc    1680
gaggacgtaa tgcgcatcac tgtgggcgtg gatggctccg tgtacaagct gcaccccagc    1740
ttcaaggagc ggttccatgc cagcgtgcgc aggctgacgc ccagctgcga gatcaccttc    1800
atcgagtcgg aggagggcag tggccggggc gcggccctgg tctcggcggt ggcctgtaag    1860
aaggcctgta tgctgggcca gtgagagcag tggccgcaag cgcagggagg atgccacagc    1920
cccacagcac ccaggctcca tggggaagtg ctccccacac gtgctcgcag cctggcgggg    1980
```

```
caggaggcct ggccttgtca ggacccaggc cgcctgccat accgctgggg aacagagcgg    2040
gcctcttccc tcagtttttc ggtgggacag ccccagggcc ctaacggggg tgcggcagga    2100
gcaggaacag agactctgga agcccccccac ctttctcgct ggaatcaatt tcccagaagg   2160
gagttgctca ctcaggactt tgatgcattt ccacactgtc agagctgttg gcctcgcctg    2220
ggcccaggct ctgggaaggg gtgccctctg gatcctgctg tggcctcact tccctgggaa    2280
ctcatcctgt gtggggaggc agctccaaca gcttgaccag acctagacct gggccaaaag    2340
ggcagccagg ggctgctcat cacccagtcc tggccatttt cttgcctgag gctcaagagg    2400
cccagggagc aatgggaggg ggctccatgg aggaggtgtc ccaagctttg aatacccca     2460 gagacctttt ctctcccata ccatcactga gtggcttgtg attctgggat ggaccctcgc    2520
agcaggtgca agagacagag cccccaagcc tctgccccaa ggggcccaca aaggggagaa    2580
gggccagccc tacatcttca gctcccatag cgctggctca ggaagaaacc ccaagcagca    2640
ttagcacacc ccaagggaca accccatcat atgacatgcc accctctcca tgcccaacct    2700
aagattgtgt gggttttta attaaaaatg ttaaaagttt taaacatg                  2748
```

RECOMBINANT VECTORS AND HOSTS COMPRISING HUMAN GLUCOKINASE ENCODING GENE

RELATED APPLICATION

This application claims priority under 35 U.S.C. §119 to Chinese Application No.: 200910000087.1, filed on Jan. 7, 2009 and is a continuation of PCT Application No.: PCT/CN2010/070038, filed on Jan. 6, 2010, respectively entitled "Gene encoding human glucokinase mutant, enzyme encoded by the same, recombinant vectors and hosts, pharmaceutical compositions and uses thereof, methods for treating and preventing diseases," at least some of which may be incorporated herein.

SEQUENCE LISTING

This application includes a sequence listing filed concurrently herewith in an ASCII text file and incorporated herein by reference. The text file, entitled "Seqlist.txt," was created on Jul. 7, 2011 and contains 8.00 KB of information. The sequence listing filed herewith is also included in the related applications referenced above.

FIELD

The disclosure is directed to a human glucokinase mutant-encoding gene; a human glucokinase mutant expressed by the gene; a recombinant vector carrying the human glucokinase mutant-encoding gene; a host comprising the recombinant vector; a pharmaceutical composition comprising one or more selected from the human glucokinase mutant-encoding gene, the human glucokinase mutant, the recombinant vector and the host; use of the human glucokinase mutant-encoding gene, the human glucokinase mutant, the recombinant vector and the host in the manufacture of a medicament for controlling blood glucose and/or a medicament for preventing and/or treating disturbances of carbohydrate metabolism; use of the human glucokinase mutant-encoding gene, the human glucokinase mutant, the recombinant vector and the host in the manufacture of a medicament for preventing and/or treating diabetes mellitus; a method for controlling blood glucose and/or preventing and/or treating disturbances of carbohydrate metabolism by use of them; and a method for preventing and/or treating diabetes mellitus by use of the same.

BACKGROUND

The glucokinase (GK) is an important member of the hexose kinase family, of which the basic biological activity is to catalyze the phosphorylation of glucose. The human glucokinase-encoding gene is located at the short arm of Chromosome 7 and comprises ten exons. The GK consists of 465 amino acids, is present specifically in mature hepatocytes and islet beta-cells, and is involved in many of key steps in glycometabolism and the secretion of insulin.

At present, it has been shown that the intensity in the in vivo insulin secretion response is proportional to the metabolic rate for glucose in insulin beta-cells. Thus, the enzyme that controls the rate of glucose influx into cells is considered as a glucose sensor regulating insulin release, and the GK is the glucose sensor in islet beta-cells. When transferred into a beta-cell through transporter 2, glucose is phosphorylated under the action of the glucokinase and introduced into the glycolytic pathway to give ATP, the amount of which is proportional to the amount of glucose introduced into the beta-cell. ATP can shut down the potassium ion channel on the plasma membrane of the beta-cell, leading to depolarization, which in turn results in calcium ion influx and eventually secretion of insulin. Since the activity of GK is controlled directly or indirectly by glucose concentration in blood, alteration in the metabolic rate for glucose within the beta-cell may regulate the secretion of insulin. Moreover, as the enzyme can also control the blood glucose concentration by facilitating synthesis of hepatic glycogen and catalyzing conversion of glucose into glucose-6-phosphate, an abnormality of GK activity plays a key role in occurrence and development of disturbances of carbohydrate metabolism.

It was found by some investigations that in patients and some animal models (e.g., fasting rats) suffering from type 2 diabetes mellitus, the GK activity in hepatocytes from rats with type 2 diabetes mellitus induced by high-fat diet is significantly reduced as compared to the normal control.

SUMMARY

The technical objective to be solved by the present disclosure is how to provide a human glucokinase mutant-encoding gene from which the human glucokinase mutant is expressed with GK activity higher than the wild-type one, so that a novel way for controlling blood glucose, treating disturbances of carbohydrate metabolism as well as diabetes mellitus, particularly type 2 diabetes mellitus, can be provided.

The present disclosure provides a human glucokinase mutant-encoding gene, the gene comprising at least one of:
(1) a nucleotide sequence as shown in SEQ ID NO: 2; or
(2) a nucleotide sequence that is identical to the nucleotide sequence shown in SEQ ID NO: 2 except the open reading frame (ORF) ranging from position 487 to 1884 of the nucleotide sequence shown in SEQ ID NO: 2, and of which the ORF encodes the same amino acid sequence as that encoded by the ORF of the nucleotide sequence shown in SEQ ID NO: 2.

It is generally believed in the prior art that because the missense mutation, nonsense mutation, and frameshift mutation at bases in the ORF of a protein-encoding gene may alter the primary structure of the amino acid sequence of a protein product encoded by the gene, only the mutation occurring within an exon of the protein-encoding gene can usually result in relatively remarkable changes in the performance of the protein product. Presently, the function for an intron of the protein-encoding gene is still unclear, and generally speaking, alteration in the intron can hardly have an essential effect on the performance of the protein product. Results of the instant disclosure have unexpectedly found that a mutant human glucokinase gene which has a mutation occurring within an intron region of the wild-type human glucokinase gene may express a human glucokinase mutant exhibiting a significantly increased GK activity in comparison to that of the wild-type.

The present disclosure also provides a human glucokinase mutant, the human glucokinase mutant-encoding gene comprising the human glucokinase mutant-encoding gene as set forth herein.

The present disclosure also provides a recombinant vector comprising a vector and a gene of interest carried thereon, the gene of interest comprising the human glucokinase mutant-encoding gene as set forth herein.

The present disclosure also provides a host, the host comprising the recombinant vector as set forth herein.

The present disclosure also provides a pharmaceutical composition which comprises a pharmaceutically acceptable excipient and one or more selected from a human glucokinase mutant-encoding gene as set forth herein, a human glucokinase mutant as set forth herein, a recombinant vector as set forth herein, and a host as set forth herein.

The present disclosure also provides use of a human glucokinase mutant-encoding gene as set forth herein, a human glucokinase mutant as set forth herein, a recombinant vector as set forth herein, and/or a host as set forth herein in the manufacture of a medicament for controlling blood glucose and/or a medicament for preventing and/or treating disturbance of carbohydrate metabolism.

The present disclosure also provides for the use of a human glucokinase mutant-encoding gene as set forth herein, a human glucokinase mutant as set forth herein, a recombinant vector as set forth herein, and/or a host as set forth herein in the manufacture of a medicament for preventing and/or treating diabetes mellitus.

The present disclosure also provides a method of controlling blood glucose or preventing and/or treating disturbances of carbohydrate metabolism, wherein an agent selected from the group consisting of a human glucokinase mutant-encoding gene as set forth herein, a human glucokinase mutant as set forth herein, a recombinant vector as set forth herein, and a host as set forth herein is administered to a patient in need thereof.

The present disclosure also provides a method of preventing and/or treating diabetes mellitus, wherein an agent selected from the group consisting of a human glucokinase mutant-encoding gene as set forth herein, a human glucokinase mutant as set forth herein, a recombinant vector as set forth herein, and a host as set forth herein is administered to a patient in need thereof.

The human glucokinase mutant expressed by a gene of the present disclosure exhibits an activity significantly higher than that of the wild-type, thus providing a novel, effective means for controlling blood glucose and/or for preventing and treating disturbances of carbohydrate metabolism, especially diabetes mellitus, for example.

DESCRIPTION

The present disclosure provides a gene encoding of a human glucokinase mutant, the gene comprising at least one of:

(1) a nucleotide sequence as shown in SEQ ID NO: 2; or
(2) a nucleotide sequence which is identical to the nucleotide sequence shown in SEQ ID NO: 2 except the open reading frame (ORF) ranging from position 487 to 1884 of the nucleotide sequence shown in SEQ ID NO: 2, and of which the ORF encodes the same amino acid sequence as that encoded by the ORF of the nucleotide sequence shown in SEQ ID NO: 2.

Preferably, the human glucokinase mutant-encoding gene has the nucleotide sequence shown in SEQ ID NO: 2. A gene encoding the human glucokinase can be isolated from leukocytes of a healthy human body, which has the nucleotide sequence shown in SEQ ID NO: 1 of the sequence listing (e.g., the wild-type gene) encoding the human glucokinase (GenBank access number BC001890, M88011, NM033508, and NM033507). The nucleotide sequence of the human glucokinase mutant-encoding gene according to the present disclosure as shown in SEQ ID NO: 2 had a deletion of one C base at position 2643 in comparison with that of the wild-type gene.

It should be understood that one skilled in the art may synthesize a nucleotide sequence different from SEQ ID NO: 2 while encoding the human glucokinase mutant of the present disclosure, according to the codon-degeneracy and the codon usage bias in different species. That is, it is a nucleotide sequence which is identical to the nucleotide sequence shown in SEQ ID NO: 2 except the open reading frame ranging from position 487 to 1884 of the nucleotide sequence shown in SEQ ID NO: 2, and of which the ORF encodes the same amino acid sequence as that encoded by the ORF of the nucleotide sequence shown in SEQ ID NO: 2.

The present disclosure also provides a human glucokinase mutant, the human glucokinase mutant-encoding gene comprising a human glucokinase mutant-encoding gene as set forth herein.

It is well known in the art that among 20 kinds of the different amino acids constituting a protein, 18 kinds of amino acids are encoded individually by 2-6 of codons, with Met (ATG) or Trp (TGG) being encoded individually by a single codon (See, Appendix D in Sambrook et al, Molecular Cloning: A Laboratory Manual, 2nd ed. New York: Cold Spring Harbor Laboratory Press, pp. 950). In other words, since the codon encoding for an amino acid is more than one in most cases due to genetic codon-degeneracy and substitution of the third nucleotide in a triplet codon often results in no changes in the amino acid composition, the nucleotide sequences encoding proteins with the identical amino acid sequence may be different. According to the well-known codon table, a person skilled in the art has acquired the nucleotide sequences aforementioned from the nucleotide sequence shown in SEQ ID NO: 2 disclosed according to the disclosure, by biological processes (e.g., PCR-based approaches, point-mutation methods) or chemical synthesis, and made use of them in recombinant techniques and gene therapies, thus this portion of the nucleotide sequences should all be included within the scope of the present disclosure. Moreover, DNA sequences disclosed herein may also be utilized by methods well known in the art, for example methods described by Sambrook et al. (Molecular Cloning: A Laboratory Manual, 2nd ed. New York: Cold Spring Harbor Laboratory Press, 1989), through modifying nucleic acid sequence provided in the present disclosure.

The present disclosure also provides a recombinant vector comprising a vector and a gene of interest carried thereon, the gene of interest comprising a human glucokinase mutant-encoding gene as set forth herein.

The genes of interest may also include a regulatory sequence, for example, a promoter, terminator, and enhancer for expression of one or more of the genes of interest. The gene of interest may also include a marker gene (e.g., genes encoding the β-galactosidase, the green fluorescent protein or other fluorescent proteins) or a gene whose product regulates expression of other genes. In addition to being a DNA, the gene of interest may also be mRNA, tRNA, or rRNA, and may also include the relevant transcription regulatory sequence usually associated with transcription of the sequence, such as, for example, a transcriptional termination signal, a polyadenylation site, and a down-stream enhancer element.

The vector may be one or more of various vectors capable of carrying the gene of interest which are commonly used in the art and/or which are available and improved by technological development. For example, the vector may comprise plasmids (naked DNA), liposomes, molecular conjugates, polymers and viruses.

The plasmid (naked DNA) may carry a gene of interest, and the plasmid carrying the gene of interest may be injected directly or introduced through gene gun, electroporation, and/or electrofusion techniques into cells in a tissue. Moreover, an ultrasonic wave may facilitate increasing the transferring efficiency for the plasmid. Ultrasonic wave in combination with microbubble echo contrast agent can increase permeability of the plasma membrane, thereby significantly increasing the transferring and expression efficiency for the naked DNA. Since this technique for permeation of plasma membrane can transiently make pores on the surface of the plasma membrane, the DNA may have a chance to be introduced into the cell.

The liposome is a droplet comprising lipid bimolecular leaflets and can mediate entry of the gene of interest through the plasma membrane. The lipid may be natural phospholipids predominating in lecithin (phosphatidylcholine, PC) and derived from egg yolk and soy bean; synthetic phospholipids, such as dipalmitoyl phosphatidylcholine (DPPC), dipalmitoyl phosphatidylethanolamine (DPPE), distearoyl phosphatidylcholine (DSPC), and so on; and/or may be comprised of cholesterol. The preferred liposome is cationic liposome, which mainly results from mixing positively charged lipids and auxiliary neutral lipids at equivalent molars. A complex can be effectively formed between the positively charged liposome and the negatively charged DNA, and transferred into cells through endocytosis.

The polymer is a stable polymer/DNA complex formed by electrical neutralization due to binding of the positive charges on a cationic polymer (e.g., poly-L-lysine) to the negative charges on the DNA. The resulting complex of the cationic polymer and the DNA, still loaded with positive charges, can bind to the negatively charged receptor on the surface of the cell, and then be introduced into the cell.

The molecular conjugate is the entity in which an exogenous DNA gene of interest is covalently bound onto a ligand, a monoclonal antibody, and/or a viral envelope protein against a specific receptor on the cell surface and the exogenous gene is introduced into a particular type of the cell by the specific binding property.

Since a virus usually can enter into a particular cell type with high efficiency, express its own proteins, and generate nascent virions, the modified virus serves first of all as a vector for gene therapy. For example, mention may be made of retrovirus vector, adenovirus vector, adeno-associated virus vector, herpes simplex virus vector, etc. Among them, the adeno-associated virus belongs to non-pathogenic member from Parvoviridae family, which can be proliferated exclusively dependent on a helper virus. The adeno-associated virus has a very small genome. For example, the adeno-associated virus type 2 has a single-chained DNA genome consisting of 4681 nucleotides, which comprise two genes, i.e. the rep gene (encoding proteins responsible for regulating viral replication, expression of structural genes and integration into the host's genome) and the cap gene (encoding the structural capsid protein), with one terminal repeat of 145 bp present at one terminus of the genome. The adeno-associated virus can infect cells in the dividing phase and in the stationary phase, and can be inserted into the chromosome of host cell, or be stably expressed for a long term in the form of an extrachromosomal concatemer DNA. It can effectively transform cell types of brain, skeletal muscle, liver and so on, and possesses characteristics, such as, antigenicity, low toxicity, non-pathogenicity, etc.

Preferably, the vector is selected from the group consisting of the cloning vector, the eukaryotic expression vector, the prokaryotic expression vector, and the shuttle vector (e.g., the shuttle plasmid pShuttle2) to implement amplification and expression of the gene of interest. When used in gene therapy, an inducible expression vector is preferably used, for example, pIRES2-EGFP. More preferably, the vector is selected from the group consisting of the pIRES2-EGFP, pCMVp-NEO. BAN, pEGFT-Actin, and an adenovirus vector. The most preferred vector is the adenovirus vector. The adenovirus is a non-enveloped virus with a linear double-stranded DNA genome, exists extensively in nature, and is classified into at least more than 100 serotypes. The adenovirus genome is about 36 kb in length and has one reverse terminal repeat respectively at one of both terminuses with a virus packaging signal being inner. There are four early transcription units (E1, E2, E3, and E4) responsible for regulation and one late transcription unit responsible for encoding viral structure proteins in the adenovirus genome. As a vector for gene therapy, the adenovirus vector has the following advantages: 1) has relatively large packaging capacity for a exogenous gene, thus being possible to insert a large fragment of the exogenous gene, up to 35 kb in length; 2) has high infection efficiency, thus being possible to efficiently transduce various cell-types in human tissues with an in vitro experimental transduction efficiency of approximately 100%; 3) can transduce the non-dividing cells; 4) yields the recombinant virus with high titers in cell culture; 5) enters into a host cell without integration into the genome of the host cell and only is transiently expressed, thus exhibiting relatively high safety. At present, the newest version of the adenovirus vector has all of (e.g., a non-viral vector) or most of adenovirus genes (e.g., a mini-adenovirus vector) deleted, and only the reverse terminal repeats and the packaging signal sequence retained, so a gene up to 35 kb in length can be inserted into the vector, a weaker cellular immune response can be elicited by the vector, a nuclear matrix attachment region introduced into the vector can allow the exogenous gene to be expressed for a long time and can increase the stability of the vector.

The present disclosure also provides a host, the host comprising a recombinant vector as set forth herein. On one hand, transformation of a host with the recombinant vector comprising the human glucokinase mutant-encoding gene of the present disclosure may be used to investigate the relation between the human glucokinase mutant and glycometabolism as well as the insulin secretion. On the other hand it may be used to prepare the active glucokinase mutant. It is preferred that the host is selected from one or more of E coli, 293 cells, min-6 cells, and human islet beta-cells. Among them, the E. coli, as a genetic engineering strain, may both comprise the recombinant cloning vector of the present disclosure to implement amplification of the human glucokinase mutant-encoding gene of the present disclosure and comprise the recombinant expression vector of the present disclosure to implement expression of the human glucokinase mutant of the present disclosure in a large amount. When the recombinant vector is a recombinant adenovirus vector, the vector may be amplified in 293 cells. The min-6 cell is a mouse islet beta-cell strain with relatively potent ability to secrete insulin, and can act as the host for the eukaryotic expression vector of the present disclosure to produce the presently disclosed human glucokinase mutant and test the GK activity thereof. The human islet beta-cell may be a commercially available cell line and also be human islet beta-cells of subjects for example from patients with diabetes mellitus. During the course of the gene therapy, it is preferred that the human islet beta-cells from a subject be retransplanted into the subject after being transduced with a human glucokinase mutant-encoding gene of the present disclosure, for avoidance of the subsequent immunological rejection.

The present disclosure also provides a pharmaceutical composition which comprises a pharmaceutically acceptable excipient and one or more selected from a human glucokinase mutant-encoding gene as set forth herein, a human glucokinase mutant as set forth herein, a recombinant vector as set forth herein, and a host as set forth herein.

The pharmaceutically acceptable excipient refers to non-toxic solid, semi-solid, or liquid fillers, diluents, coating materials or other auxiliary agents for formulations, for example, including, but not limited to saline, buffered saline, glucose, water, glycerol, ethanol, and mixtures thereof. The pharmaceutical composition is suitable for parenteral, sublingual, intracisternal, intravaginal, intraperitoneal, intrarectal, intrabuccal, or transepidermal administration.

The parenteral administration includes intraveinous, intramuscular, intraperitoneal, intrathoracic, subcutaneous, intra-articular injection and infusion. The pharmaceutical composition suitable for parenteral administration includes aqueous or non-aqueous sterile solutions, dispersions, suspensions or emulsions, and powders formulated in an injectable sterile solution or dispersion immediately before use. Appropriate aqueous or non-aqueous carriers, diluents, solvents or excipients include water, ethanol, glycerol, propylene glycol, polyethylene glycol, carboxymethyl cellulose, vegetable oils and injectable organic esters, such as, ethyl oleate. These compositions may also comprise preservatives, wetting agents, emulsifiers, protectants and dispersion aids, for example, inositol, sorbitol, and sucrose. It is preferred to add osmotic regulators such as carbohydrates, sodium chloride, and potassium chloride.

Transepidermal administration includes administration on the skin, mucosa, and the surface of the lung and the eye. Such a pharmaceutical composition includes pulveres, ointments, drops, transdermal patches, Iontophoresis devices, inhalants, etc. The composition for intrarectal or intravaginal administration is preferably a suppository, which can be prepared by mixing the recombinant vector of the present disclosure with appropriate non-stimulatory excipients, such as cacao butter, polyethylene glycol, or suppository wax base, wherein the excipient or carrier remains solid at room temperature, and become liquid at body temperature, thus being melt in the rectum or vagina and releasing the active compound.

Preferably, the pharmaceutical compositions is an injection which comprise a pharmaceutically acceptable excipient and one or more selected from a human glucokinase mutant-encoding gene as set forth herein and a recombinant vectors as set forth herein.

The said pharmaceutically acceptable excipient is a phosphate buffer with a pH value of 4.0-9.0; and $10^2$-$10^{10}$ copies of the human glucokinase mutant-encoding gene or $10^2$-$10^{10}$ copies of the recombinant vector comprised in one milliliter of the injection.

The injection further comprises a protectant and/or an osmotic regulator; the content of the protectant is 0.01-30% by weight on basis of the injection, the protectant is one or more selected from inositol, sorbitol, and sucrose; the content of the osmotic regulator allows osmotic pressure of the injection to be 200-700 mOsm/kg with the osmotic regulator being sodium chloride and/or potassium chloride.

When the injection was used in the administration, the subject was administered with the injection containing $10^2$-$10^{10}$ copies, preferably $10^5$-$10^8$ copies, and more preferably $10^6$-$10^8$ copies of the human glucokinase mutant-encoding gene; or containing $10^2$-$10^{10}$ copies, preferably $10^5$-$10^{10}$ copies, and more preferably $10^6$-$10^{10}$ copies of the recombinant vector; It is further preferred that the recombinant vector is a recombinant adenovirus vector which is administered in the amount ranging from $10^3$-$10^{10}$ plaque forming units (pfu), preferably $10^5$-$10^{10}$ pfu, and more preferably $10^6$-$10^{10}$ pfu. When the pharmaceutical composition of the present disclosure is injected, the injection dosage may be the one commonly used in the art, at most 500 μL, typically 1-200 μL, preferably 1-10 μL; however, a dosage of up to 10 mL may also be used depending on the injection site. Since one skilled in the art is able to readily determine the optimal route of administration and dosages, the routes of administration and dosages above are for reference only. The dose may be determined according to various parameters, especially the age, body weight of the patient to be treated, severity of the disease, disorder, or condition as well as and the route of administration. The injection of the pharmaceutical composition as set forth herein may also be administered systematically, and the injection of the pharmaceutical composition of the present disclosure may also be injected into a local site (e.g., into skeletal muscle).

The present disclosure also provides use of a human glucokinase mutant-encoding gene as set forth herein, a human glucokinase mutant as set forth herein, a recombinant vector as set forth herein, and/or a host as set forth herein in the manufacture of a medicament for controlling blood glucose and/or a medicament for preventing and/or treating disturbance of carbohydrate metabolism.

The present disclosure also provides use of a human glucokinase mutant-encoding gene as set forth herein, a human glucokinase mutant as set forth herein, a recombinant vector as set forth herein, and a host as set forth herein in the manufacture of a medicament for preventing and/or treating diabetes mellitus.

The present disclosure also provides a method of controlling blood glucose and/or for preventing and/or treating disturbances of carbohydrate metabolism, wherein an agent selected from the group consisting of a human glucokinase mutant-encoding gene as set forth herein, a human glucokinase mutant as set forth herein, a recombinant vector as set forth herein, and a host as set forth herein is administered to a patient in need thereof.

The present disclosure also provides a method of preventing and/or treating diabetes mellitus, wherein an agent selected from the group consisting of a human glucokinase mutant-encoding gene as set forth herein, a human glucokinase mutant as set forth herein, a recombinant vector as set forth herein, and a host as set forth herein, is administered to a patient in need thereof.

The following examples will further illustrate the disclosure of the present disclosure, and should not be construed in any way to limit the present disclosure. All of modifications or replacements that may be made to the methods, acts, and/or conditions in the present disclosure without departing from the spirit and essence of the present disclosure fall within the scope of the present disclosure including the appended claims. The technical means used in the examples are conventional means well-known to one skilled in the art, unless specifically stated otherwise. All of reagents and culture media used in the present disclosure are commercially available products unless specifically specified otherwise.

Example 1

Chemical Synthesis of a Human Glucokinase Mutant-Encoding Gene (G262) of the Present Disclosure The human glucokinase mutant-encoding gene with the nucleotide sequence as shown in SEQ ID NO: 2, has a full-length of 2748 bps. After sequence analysis, it was shown that there are three unique restriction sites, HindIII, SacI, and BamHI, which are located at the position 2443, 1327, and 2250 of SEQ ID NO: 2, respectively. The synthesis strategy was as follows: synthesis of the partial DNA fragments respectively using the solid phase phosphoramidite triester approach, ligation of the synthesized fragments, sequencing and verification of the ligated gene, and correction of the mistaken ligation, in which the detailed acts were the following:

1. An A fragment with a total of 1360 bps ranging from the 5' terminus to the Sac I restriction site of the gene was synthesized;

2. Results from the sequencing and identification indicated that the whole A fragment was obtained from act 1, the whole fragment was subjected to terminal modification and then ligated between the HindIII/SacI sites of the vector PCR2. I (Invitrogen, Co.);

3. A B fragment with a total of 939 bps ranging from the SacI restriction site to the BamHI restriction site of the gene was synthesized;

4. Results from the sequencing and identification indicated that the whole B fragment was obtained from act 3, the whole fragment was subjected to terminal modification and then ligated between the BamHI/SacI sites of the vector PCR2. I;

5. A C fragment with a total of 551 bps ranging from the BamHI restriction site to 3' terminus of the gene was synthesized;

6. Results from the sequencing and identification indicated that the whole C fragment was obtained from act 5, the whole fragment was ligated into the vector comprising the B fragment, resulting in a D fragment of a total of 1457 bps.

7. Results from the sequencing and identification indicated that the whole D fragment was obtained from act 6. The A and D fragments to be ligated were digested with the SacI restriction enzyme to produce DNA fragments with a cohesive end, a DNA ligation reaction was carried out in which the T4 DNA polymerase was involved. The human glucokinase mutant-encoding gene with the nucleotide sequence as shown in SEQ ID NO: 2, was obtained eventually. All of enzymes and buffers used were purchased from Clontech, Co. and restriction digestion and ligation were performed according the protocol provided by Clontech, Co.

Since there were some protective sequences at all of the terminuses of the synthesized fragments to facilitate terminal modification of the fragments after being synthesized, the length of the synthesized sequence was a little longer than the actual length. The protective sequence refers to a protective sequence of 8 to 20 bases which is added artificially to either side of a terminal restriction site present at the end of a DNA in order to eliminate the inability of a restriction enzyme to normally bind to and cleave the DNA at the restriction site in presence of the steric hindrance, the protective base sequence being from Clontech Co. the manufacturer for restriction enzymes. If the DNA strands would be degraded first from its terminus, the presence of the protective bases can protect the restriction site from being damaged during the manipulation. The modification refers to a process in which the DNA fragment is enzymatically digested with a restriction enzyme to remove the protective bases. The restriction enzyme and T4 ligase utilized as well as the reaction buffers and experimental systems utilized were all from Clontech Co, which provided the introduction of the corresponding products and the standard operation protocols thereof at its website (http://www.clontech.com/).

The gene sequence correctly ligated in act 7 was amplified by PCR, and the sequencing result of the gene was consistent with SEQ ID NO: 2. The resulting gene was stored at −20° C. for ligation into an expression vector.

Comparative Example 1

Preparation of a Human Wild-Type Glucokinase-Encoding Gene (G261)

The human wild-type glucokinase-encoding gene was prepared according to the nucleotide sequence as shown in SEQ ID NO: 1 with reference to the protocol in Example 1.

Example 2

Figure 3:
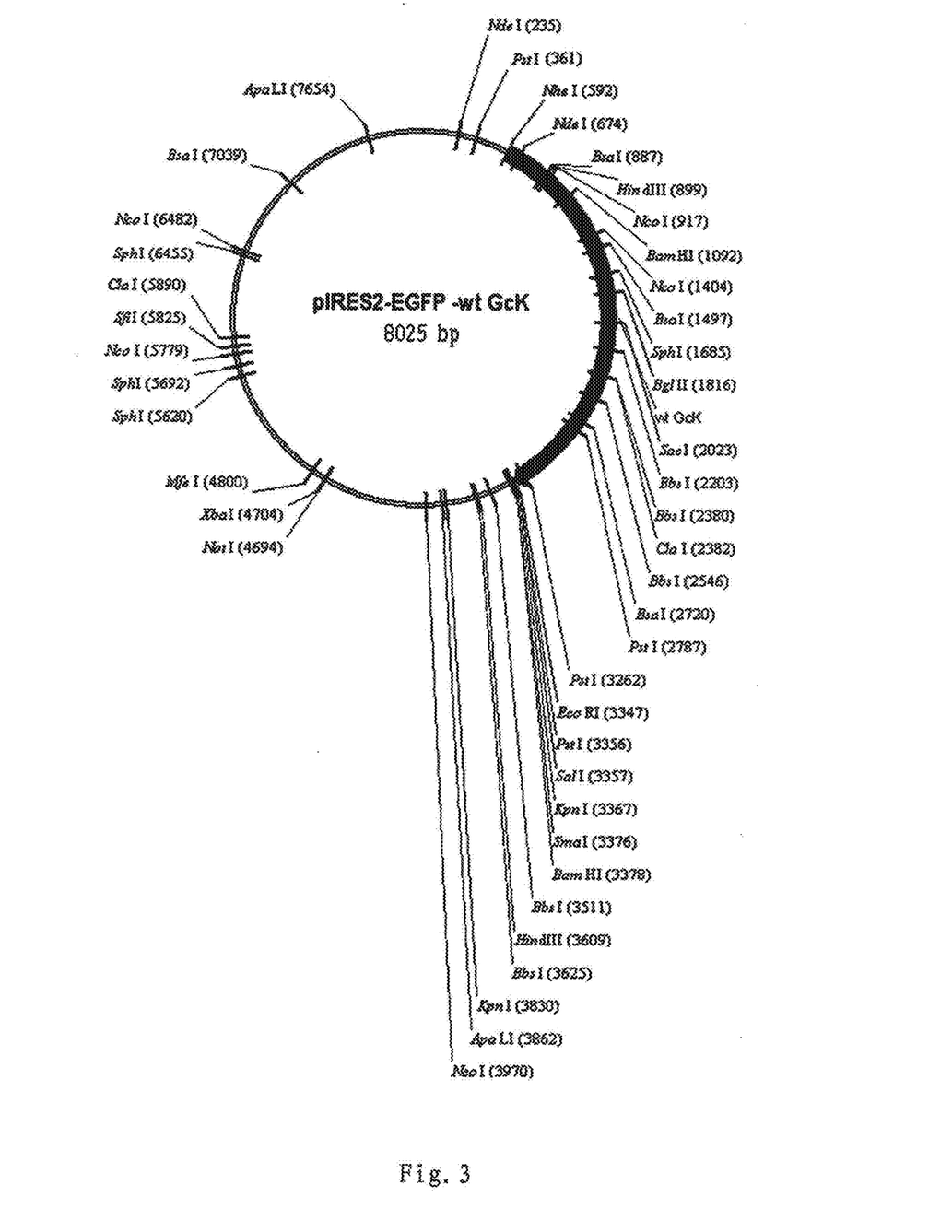
FIG. 3 is a schematic representation for the structure of a pIRES2-EGFP plasmid vector.

Construction of an Expression Vector 1-1) Linearization of the pIRES2-EGFP plasmid vector The pIRES2-EGFP plasmid is a circular structure (see, in FIG. 3) and needs to be linearized before it is transferred into cells. The BstBI restriction enzyme (TTCGAA) (New England Biolabs, NEB Co.) was selected, because the enzyme has a unique restriction in the plasmid and thus restriction digestion has no effect on the protein expression. The IRSE means to an internal ribosome entry site characterized in that, when the IRSE is present after an ORF, another coding sequence following the IRSE is allowed to be translated after translation of the ORF would have been terminated. Thus, the two protein-encoding genes individually having an independent ORF were expressed as a fusion protein.

| | |
|---|---|
| pIRES2-EGFP plasmid DNA | 10 μg, |
| Restriction digestion buffer | 5 μL, |
| Restriction enzyme | 10 Units, and |
| Deionized water | made the system up to 50 μL | were incubated at 37° C. for 3 hours, subjected to phenol/chloroform extraction to give the total DNA, precipitated by anhydrous ethanol to yield a DNA pellet. The DNA pellet was washed with 70% ethanol and re-dissolved in deionized water. A 1.2% agarose gel electrophoresis was performed to detect the molecular weight of the plasmid and purify the linearized pIRES2-EGFP plasmid vector. The purified plasmid was stored at −20° C. until used.

1-2) Ligation of the linearized pIRES2-EGFP plasmid and the gene of interest

Figure 1:
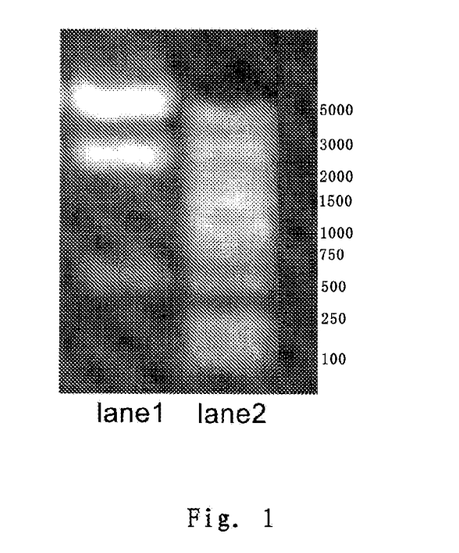
FIG. 1 is an electrophoresis photograph obtained after ligation of a linearized pIRES2-EGFP plasmid and a gene of interest (e.g., Example 1).

| | |
|---|---|
| The recovered linear pIRES2-EGFP plasmid vector | 0.3 μg, |
| DNA of the gene of interest (in Example 1 or Comparative Example 1) | 3 μg, |
| T4 ligase | 10 units, |
| Ligation buffer | 1.0 μL, and |
| Deionized water | and made the system up to 10 μL, | were incubated at 14° C. for 12 hours, subjected to phenol/chloroform extraction to give the total DNA, precipitated by anhydrous ethanol to yield a DNA pellet. The DNA pellet was washed with 70% ethanol and re-dissolved in deionized water. The molecular weight of the plasmid was identified by electrophoresis (see FIG. 1 for the electrophoresis result of Example 1, wherein lane 1 is the electrophoresis result for the ligated total DNA of Example 1, lane 2 is the molecular weight size marker, and the band with a molecular weight greater than 5000 in lane 1 is the successfully ligated band) to and the pIRES2-EGFP plasmid vectors carrying the genes of interest (in Example 1 or Comparative Example) were individually purified and recovered. The purified plasmid was stored at −20° C. until used.

The restriction enzyme and T4 ligase utilized as well as the reaction buffers and experimental systems utilized were all from NEB Co, and manipulated according to the introduction of the corresponding products and the standard operation protocols thereof.

2) Construction of an adenovirus expression vector.

2-1) The human adenovirus serotype 5 and the E1/E3-deleted adenovirus were chose in the Example to construct a recombinant shuttle plasmid vector in the following acts.

a) A shuttle plasmid pShuttle2-CMV (BD Co.) was provided (CMV denotes the cytomegalovirus);

b) The plasmid in act a) was double-digested with restriction enzymes EcoRV+NotI;

c) Terminal dephosphorylation was performed with calf intestinal alkaline phosphatase (CIP);

d) A vector fragment of 3.4 kb was recovered;

e) The pIRES2-EGFP plasmid vector obtained in the acts 1-2 above was double-digested with restriction enzymes EcoRV+NotI, and the G262-IRES2-EGFP or G261-IRES2-EGFP resulting from the restriction digestion was respectively ligated into the shuttle plasmid vector fragment obtained in the act d) in presence of T4 ligase, thus generating the recombinant circular shuttle plasmid pShuttle2-CMV-G262-IRES2-EGFP or the recombinant circular shuttle plasmid pShuttle2-CMV-G261-IRES2-EGFP;

f) The shuttle plasmids obtained in act e) were digested with the restriction enzyme NheI,     g) The enzymatically cleaved terminuses in the act f) were filled in with Klenow fragment of DNA polymerase I;

h) A fragment of 4.1 kb was recovered (the fragment is a DNA fragment into which the exogenous gene was inserted and of which partial sequences from the vector were located at both terminuses).

2-2) Identification of the circular shuttle plasmid pShuttle2-CMV-G262-IRES2-EGFP or the circular shuttle plasmid pShuttle2-CMV-G261-IRES2-EGFP obtained.

Figure 6:
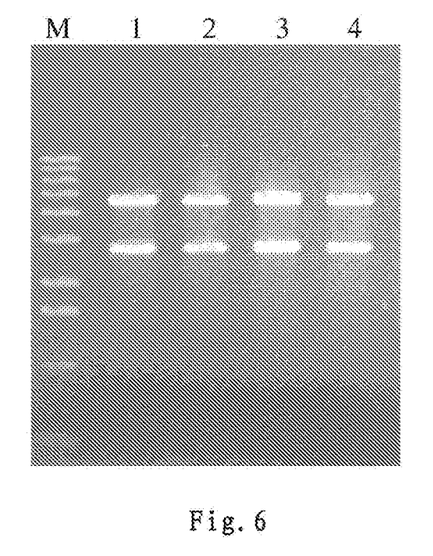
FIG. 6 is an electrophoresis photograph for identification of a recombinant circular shuttle plasmid pShuttle2-CMV-G262-IRES2-EGFP or a recombinant circular shuttle plasmid pShuttle2-CMV-G261-IRES2-EGFP.

The circular shuttle plasmid pShuttle2-CMV-G262-IRES2-EGFP or pShuttle2-CMV-G261-IRES2-EGFP was enzymatically cleaved with EcoRI. The resulting product from the restriction digestion was identified on a 1.2% agarose gel electrophoresis; The positive clone would yield two bands with molecular weight of 4.7 kb and 2.8 kb, respectively, while the negative clone would yield one band of 3.4 kb only. The identification result was shown in FIG. 6, wherein M is a molecular weight size marker (the bands in the 1 kb DNA ladder from top to bottom were 8 kb, 7 kb, 6 kb, 5 kb, 4 kb, 3 kb, 2 kb, 1.6 kb, 1 kb, 517 bp, 396 bp, and 230 bp, respectively), Lanes 1-4 (two samples of pShuttle2-CMV-G261-IRES2-EGFP and two samples of pShuttle2-CMV-G262-IRES2-EGFP) all represented the positive clones.

2-3) The CMV-GFP-IRES-GFP was transferred from pShuttleGFP-CMV-TrkC onto the pAd adenovirus vector, generating the recombinant adenovirus plasmid pAd-GFP-G261 or pAd-GFP-G262. All of blank plasmids used above were commercial vectors purchased from Clontech Co. (http://www.clontech.com/), and the experimental conditions and the kits used were all commercial kits. The kit used in the transferring was Adeno-X Expression System 1 from Clontech (Clontech 631513), and the transferring was implemented according to the experimental protocol provided by Clontech Co.

2-4) Identification of the recombinant adenovirus plasmids pAd-GFP-G261 and pAd-GFP-G262.

Figure 7:
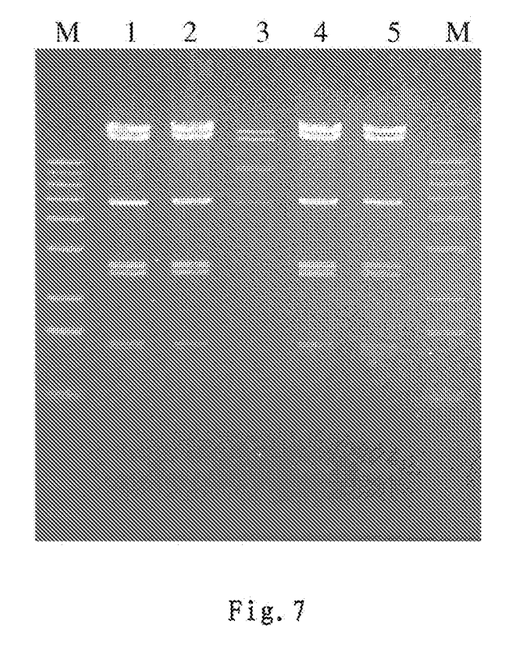
FIG. 7 is an electrophoresis photograph for identification of a recombinant adenovirus pAd-GFP-G261 or a recombinant adenovirus pAd-GFP-G262.

Restriction digestion with XhoI was performed on the recombinant adenovirus plasmids pAd-GFP-G261 and pAd-GFP-G262, respectively. The resulting product from the restriction digestion was identified on a 1.2% agarose gel electrophoresis; the positive clone would yield bands with the following molecular weight of 14 kb, 11.8 kb, 4.9 kb, 2.6 kb, 2.47 kb, 1.45 kb, and 0.6 kb, respectively, while the negative clone would yield bands with the following molecular weight of 14 kb, 11.8 kb, 4 kb, 2.47 kb, 1.45 kb, and 0.6 kb, respectively. The identification result was shown in FIG. 7, wherein M is the molecular weight size marker (the bands in the 1 kb DNA ladder from top to bottom were 8 kb, 7 kb, 6 kb, 5 kb, 4 kb, 3 kb, 2 kb, 1.6 kb, 1 kb, 517 bp, 396 bp, and 230 bp, respectively), Lanes 1-5 (two samples of the recombinant adenovirus plasmid pAd-GFP-G261 and three samples of the recombinant adenovirus plasmid pAd-GFP-G262) all represented the positive clones.

2-5) Packaging, amplification, harvest and purification of the recombinant adenovirus.

The recombinant adenovirus DNA correctly identified in acts 2-4) was transfected into 293 cells for being packaged and then the virus stock was stored. The packaged adenovirus was amplified and then the virus stock was stored (secondary virus stock). Moreover, the amplified secondary virus stock was subjected to two cycles of large-scale amplification. After the amplification was complete, the virus was harvested and subjected to CsCl density-gradient centrifugation for purification, and the residual CsCl in the virus solution was removed by dialysis.

The detailed manipulation was as follows:

a) 293 cells (the E1-transformed human embryonic kidney cell) were seeded in one or two cell-culture dishes (60 mm) 24 hours before the transfection, and grown to a confluency rate of 50-70% when transfected.

b) Prior to the transfection, the plasmid of interest was enzmatically cleaved with Pac I (6 μg DNA per a 60 mm cell culture dish). The enzmatically cleaved plasmid was precipitated by ethanol and re-dissolved in 20 μL of sterile water.

c) The cells were transferred with 6 μg of PacI-treated plasmid using PEI or other transfection agents.

d) After 8 hours of transfection, the transfection mixed liquor was removed and 4 mL of DMEM complete culture medium (containing 10% CBS and 1% Pen/Strep) was added.

e) After 7 to 10 days of the transfection, the cells were scraped off the culture dish and transferred into a 50 mL conical tube. After centrifuged, the cells were resuspended in 2.0 mL of PBS or the complete culture medium. The suspension was frozen in liquid nitrogen and thawed in a 37° C. water bath with sharp shaking. The act was repeated four times. After centrifugation, the resulting supernatant was stored at −20° C.

f) The 293 cells were seeded into a 60 mm cell culture dish, cultured to a confluency rate of 50-70%, and inoculated with virus-containing supernatant in volume percent of 30-50%. The apparent cellular lysis and the cytopathic effect (CPE) were observed 3 days post the infection.

g) When ⅓ to ½ of the cells detached off and floated up, which was usually 3-5 days post the infection, the virus was collected. The presence of the recombinant adenovirus can be further confirmed by Western blot or PCR (5 μL of the virus-containing supernatant was added into 10 μL of PCR-grade protease K and incubated at 55° C. for 1 hour; then, the mixed sample was boiled up for 5 minutes and centrifuged; 1-2 μL of the resulting supernatant was used in a PCR reaction).

h) The virus-containing supernatant was collected following the protocol in act f). In this case, a virus stock with a viral titer of at least $10^7$ virions/mL (infectious particles/mL) can typically be collected. Each cycle of the amplification was to elevate the viral titer one order of magnitude.

i) For further amplification, the virus-containing supernatant obtained in act h) was further inoculated into the cells in a 100 mm cell culture dish, the resulting virus was collected according the protocol in act f) and inoculated into the 293 cells in a 150 mm cell culture dish to obtain sufficient amount of the progeny virus.

j) 15% of CsCl and 40% of CsCl solutions were sequentially added into a Beckman centrifugation tube to form a CsCl-gradient solution.

k) The virus-containing supernatant with eventually-enriched virions was dropped onto the CsCl-gradient solution.

l) An ultracentrifugation was performed at 30000 rpm at 4° C. for 16 hours.

m) There were two bands after the centrifugation. The upper band with a fainter color contained primarily empty adenovirus capsids without infectivity; while the lower band with a brighter color contained live virions in need of being collected. The lower band was collected with a 16-gauge needle.

n) The collection was dialyzed against a TBS (10 mM Tris, 0.9% NaCl, pH 8.1) for 1 hour and then against the TBS containing 10% glycerol two times (one hour per time) to remove CsCl.

o) The purified adenovirus was aliquoted into EP tubes.

p) The quantity of the total protein in the dialysate was determined in an Eppendorf spectrophotometer (Eppendorf Biophotometer) with 1 μg of viral protein corresponding to $4 \times 10^9$ virions.

q) For long term storage, stored at −70° C., for short term storage, at 4° C.; the amount of the reserve stock was not less than 1E+11 VP units/aliquot container after aliquoting; the above-described large-scale amplification means to attain the amount of the virus over 1E+12 VP units/aliquot container.

r) Since there is difference in infection efficiency of the adenovirus for different cell lines and cytotoxic effect of the virion is taken into account, the viral dosage needed is determined usually by serial gradient dilution method.

The target cells were infected with the virion in relative amount to cell number 1:1, 10:1, 100:1, and 1000:1; Polybrene (1,5-dimethyl-1,5-diazaundecamethylene polymethobromide) was added in relative volume to the medium 1:1000. The plate was centrifuged at 37° C. for 30 min.

s) The medium was replaced 8-12 hours post infection and the virus was collected.

2-6) Quality control on packaging of the recombinant adenovirus.

The total amount of infectious virus $\geq 1.05 \times 10^{12}$ PFU/3 mL.

2-7) Storage of the recombinant adenovirus

Storage buffer: 4% sucrose, 2 mM $MgCl_2$, 10 mM Tris, pH 8.0

Storage temperature: −80° C.

Example 3

Transfection of the Min-6 Cell

1. The basal medium for min-6 cells:

| | |
|---|---|
| DMEM (Gibco 11995) | 830 mL |
| FBS(Gibco. US) | 150 mL |
| P/S | 10 mL |
| Hepes (1M) | 10 mL |
| β-mercaptoethanol | 10 μL |

The Petri dishes had their surface not treated for cell cultivation and were all ficol flasks.

Incubation conditions: 37° C.; 5% $CO_2$; 95% relative humidity.

The pIRES2-EGFP plasmid vectors prepared in Example 2 carrying the gene of interest (Example 1 or Comparative Example 1) were transfected into a min-6 cell line according to the Lipofectmine 2000 (invitrogen) protocol. The detailed acts were as follows:

Day 1: The cells frozen in liquid nitrogen were revived and seeded in a 25 $cm^2$ culture flask.

Day 2: The culture medium is replaced.

Day 3: The cells were digested with a 0.2% trypsin solution (Gibco) once grown to confluency rate of 90% and seeded into a 6-well plate at a density of $2 \times 10^5$ cells/mL (with the antibiotic withdrawn at this time).

Day 4: 4 μg of the linearized vectors, 10 μL of Lipofectmine, and Opti-M up to 100 μL were mixed and left alone at room temperature for 10 minutes. All of the mixture was added into the culture media for min-6 cells and mixed gently to homogenicity. The resulting mixture was left alone at 37° C. in 5% $CO_2$ at 95% relative humidity for 24 hour. At same time, a negative control was set up.

Day 5: The culture medium is replaced. (The culture media containing the antibiotic can be used alternatively).

Figure 5:
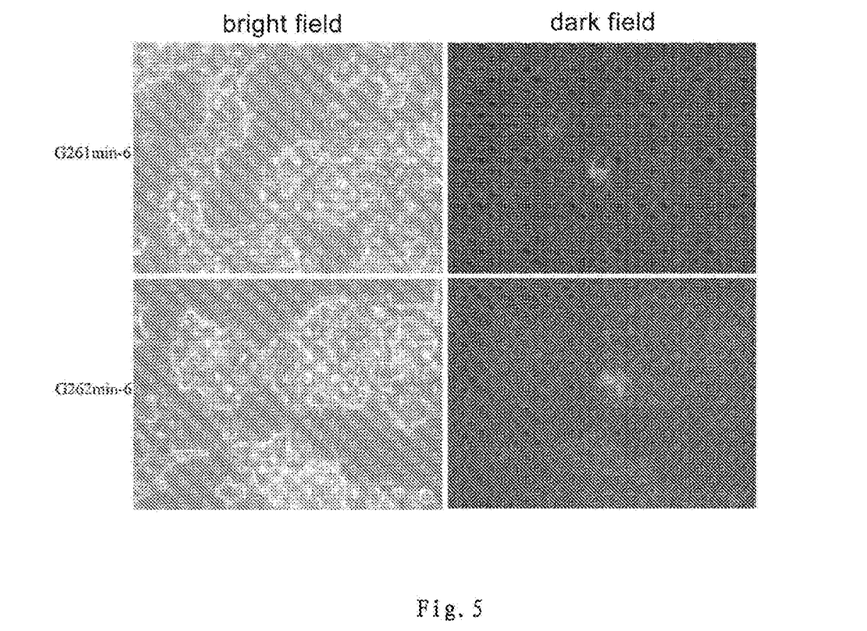
FIG. 5 is a microscopic photograph for min-6 cells successfully transferred with a recombinant plasmid vector.

Day 6: The culture medium is replaced and supplemented with the antibiotic G418 (400 ug/mL) to screen the stably transfected cell lines (see in FIG. 5, It was observed under a dark field that the green fluorescent protein had been expressed) for 8 successive days.

After a cell line stably expressing the exogenous GCK protein was screened out, it was identified at its genomic level by PCR. For this purpose, a pair of primers specific to the vector sequence (forward primer: 5'-GCGGAGAAGCCT-TGGATATT-3'; reverse primer: 5'-TTTGATAGCGTCTCG-CAGAA-3') was designed, and it was confirmed by experiments and sequence alignment that the primers were unable to initiate amplification from the genome of a min-6 cell line, but able to produce a 653 bp-sized amplicon from the introduced vector. A pair of primers specific to the min-6 genome (forward primer: 5'-CAAGCCCTGTAAGAAGCCACT-3'; reverse primer: 5'-TGCTTCCAGCTA CTTGAGGTC-3') was also designed, and it was also confirmed by experiments and sequence alignment that the primers were unable to amplify any specific product from the introduced vector and able to produce a 956 bp-sized product from the genome of a min-6 cell line.

Figure 4:
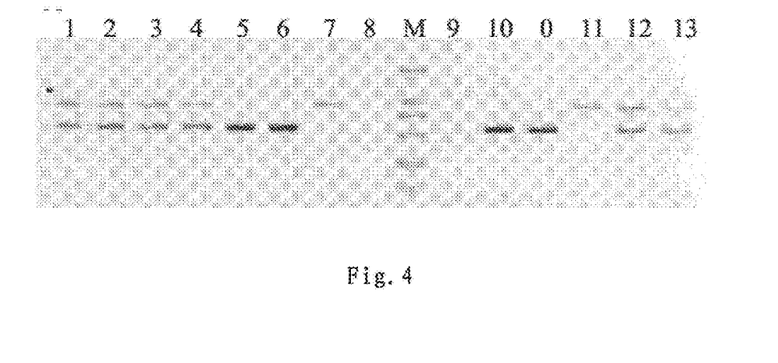
FIG. 4 is an electrophoresis photograph for identification of min-6 cells successfully transferred with a recombinant plasmid vector.

Therefore, two amplified products with different size can be observed after amplification of the min-6 genome carrying the exogenous DNA (See in FIG. 4).

Extraction of genomic DNA of min-6 cells
Formulation of the reagents in need:
 Proteinase K lysis buffer (Porteinase K buffer SNET)
 20 mmol/L Tris-Cl (pH 8.0)
 5 mmol/L EDTA (pH 8.0)
 400 mmol/L NaCl
 1% (m/v) SDS
 400 μg/mL Proteinase K The cells were digested with pancreatic proteinases before extraction of genomic DNA according to the following acts:

A The proteinase was added and incubated at 56° C. overnight.
B Anhydrous ethanol in two time volumes was added and shaken evenly to homogenicity.
C The resulting mixture was left alone at −80° C. in a refrigerator.
D Centrifugation at 12000 g was performed for 15 min.
E The supernatant was discarded.
F The DNA pellet was washed with 75% ethanol.
G Centrifugation at 12000 g was performed for 10 min.
H The DNA pellet was washed with 75% ethanol.
I Centrifugation at 12000 g was performed for 10 min.
J The DNA pellet was dried up.
K The DNA pellet was dissolved in purified water.

The DNA was quantified with a UV spectrophotometer and diluted with purified water according to DNA concentration to provide a final DNA concentration of 50 ng/μL for a working solution. The stock solution was stored in a −20° C. refrigerator until ready to use, and the dilution thereof was stored in a 4° C. refrigerator and served as a PCR template useful in a PCR reaction.

PCR reaction system of 10 μL:

| | |
|---|---|
| 10 × PCR buffer ($Mg^{2+}$-free) | 1.0 μL, |
| dNTP (25 mM) | 0.2 μL, |
| $MgCl_2$ (25 mM) | 1.0 μL, |
| Primer 1(Forward/Reverse) | 1.0 pmol, |
| Primer 2(Forward/Reverse) | 1.0 pmol, |
| DMSO (Dimethyl sulfoxide) | 0.5 μL |
| AmpliTaq Gold DNA polymerase | 0.05 μL (5 U/μL), |
| Template genomic DNA (50 ng/μL) | 2.0 μL and |
| $H_2O$ | made up to 10.0 μL of the total system |

PCR TouchDown reaction programme:
1=95° C. lasting 8 min
2=94° C. lasting 30 seconds
3=68° C. lasting 1 min
−1.0° C. per cycle
4=72° C. lasting 45 seconds
5=turn to 2, 12 cycles
6=95° C. lasting 30 seconds
7=54° C. 1 lasting 5 seconds
+1 s per cycle
8=72° C. lasting 45 seconds
9=turn to 6, 30 cycles
10=72° C. lasting 60 min
11=4° C. lasting maintenance (ever)

The PCR-amplified product was identified by 1.2% agarose gel electrophoresis. The identification result was shown in FIG. 4, in which Lane 0 is: G262 plasmid, Lane 1: G261 min-6 genome, Lane 2: G261 min-6 genome, Lane 3: G262 min-6 genome, Lane 4: G262 min-6 genome, Lane 5: G261 plasmid, Lane 6: G261 plasmid, Lane 7: wild-type min-6 genome, Lane 8: negative control (water), Lane 9: negative control (water), Lane 10: G262 plasmid, Lane 11: wild-type min-6 genome, Lane 12: G261 min-6 genome, Lane 13: G262 min-6 genome, and Lane M: molecular weight size marker DNA.

2. The min-6 cells were seeded uniformly into a 12-well plate with replication in tetra wells per sample. The cells were synchronized by serum starvation: the culture supernatant was pipetted off, the cells were washed two times with sugar-free Krebs-Ringer bicarbonate buffer (KRBB) and pretreated with sugar-free KRBB+0.1% BSA for 2 h. Formulation for the medium of sugar-free KRBB+0.1% BSA was as follows:

| | |
|---|---|
| KRBB | 1 L |
| NaCl | 6.9496 g |
| KCl | 354 mg |
| $NaHCO_3$ | 420 mg |
| $MgSO_4$ | 144.4 mg |
| $KH_2PO_4$ | 160.6 mg |
| HEPES | 4.766 g |
| $CaCl_2$ anhydrous | 281.915 mg |
| PH | 7.4 |
| BSA | 0.1% (final concentration) |

3. The culture supernatant was pipetted off, and then the cells were treated with KRBB G2.8+0.1% BSA or KRBB G25+0.01% BSA for 1 hour, in which the G2.8 indicated the glucose concentration of 504.448 mg/L and G25 indicated the glucose concentration of 4.504 g/L.
4. The supernatant was collected from 3 wells and stored at −20° C. until to be assayed.
5. The cells in the fourth well were digested and counted in a hemocytometer to statistically calculate the number of the cell in each sample.
6. The intensities of insulin secretion from min-6 cells under the condition of high glucose concentrations were determined by radioimmunoassay.

In the radioimmunoassay, there is a functional relation between insulin content in the sample and $^{125}I$ cpm count in the sample. Therefore, a standard curve should to be plotted in each experiment to calculate a functional relation between insulin content and $^{125}I$ cpm count.

Preparation of a Standard Curve and Measurement of the Samples

TABLE 1 insulin content and $^{125}I$ cpm count in the standards

| | μU/mL | CPM |
|---|---|---|
| Standard 1 | 2 | 9692 |
| Standard 2 | 4 | 8191 |
| Standard 3 | 15 | 6471 |
| Standard 4 | 40 | 3636 |
| Standard 5 | 175 | 2151 |
| Standard 6 | 300 | 1519 |

Figure 2:
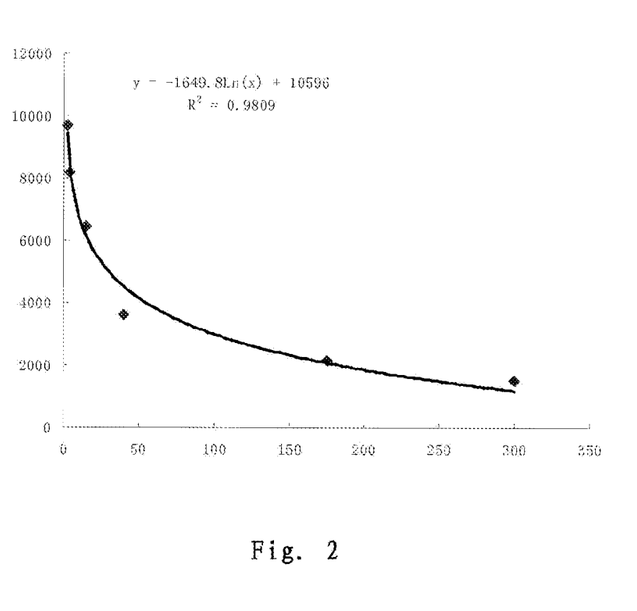
FIG. 2 is a curve for the functional relation between an insulin unit (μ unit/mL) on the X-axis and a $^{125}I$ counting on the Y-axis.

As shown in FIG. 2, based on insulin content and $^{125}$I cpm count in the standards, the functional relation between the insulin unit (μunit/mL) X and $^{125}$I count Y was established as follows:

$$y=-1649.8 \ Ln(x)+10590 \quad \text{Formula 1}$$

Thus, $$x=\exp[(10590-y)/1649.8] \quad \text{Formula 2}$$

$^{125}$I cpm counts in supernatants from the wt, G261 min-6, and G262 min-6 culture were actually determined and then were converted to amounts of the secreted insulin by calculation with Formula 2.

TABLE 2

The amount of the secreted insulin

| | μU/mL (x) | CPM (y) |
|---|---|---|
| Wt | 53.0261 | 4045 |
| G261 | 54.79043 | 3991 |
| G262 | 64.065 | 3733 |

It can be seen from Table 2 that the G262 exhibits an effect of significantly promoting the insulin secretion, which suggests that the glucokinase activity of the G262 is significantly higher than that of the wild-type.

Example 4

In Vivo Experiment of the Recombinant Adenovirus on Animals

1. Rearing of the Experimental Animal (GK Rat).

GK rats as the experimental animal were purchased from National Rodent Laboratory Animal Resources, Shanghai Branch, China. As an experimental animal, GK rats, the rats SLAC/GK suffering from the type 2 diabetes, was reared in 1975 by Tohoku University. They were established by screening the hyperglycemic individuals out from the outcrossed WISTAR rats. The female reaches sexual maturation at 8-10 week-old and male at 10-12 week-old. The gestation period lasts from 21 to 23 days, the litter size is 7-9, the conception rate is 60%, and lactation lasts for 28 days. GK rats are widely used in investigation of the non-insulin-dependent diabetes mellitus (NIDDM, type II diabetes). After onset of diabetic urine, hyperglycemia, attenuated insulin secretion, etc. appear rapidly in GK rats, being complicated by retinopathy, microangiopathy, neuropathy, nephropathy in later stages. In contrast to other rodent animal models of type II diabetes, the GK rat is a non-obese model. 20 of the 10 week-old GK rats were chosen in the Example and given ad libitum access to food and water for one week.

2. Administration of the Recombinant Adenovirus From Example 2.

(1) Formulation of the Injection:

A set of phosphate buffers were formulated respectively according to the doses shown in Table 3, and then sterilized at 121° C. for 60 min. Under sterile condition, the recombinant adenovirus stock from the acts 2-6 in Example 2 was filtrated with a millipore filter membrane of 0.45 μm. The cellular debris was removed. The filtrate was collected into a sterile centrifugation tube and centrifuged at 8000 r/min for 1 hour. The supernatant was discarded. The resulting virus pellet was dispersed into the autoclaved phosphate buffers above on the basis of the titers shown in Table 3, yielding the injections of the present disclosure.

TABLE 3

| Medicaments | Recipe 1 | Recipe 2 | Recipe 3 | Recipe 4 | Recipe 5 |
|---|---|---|---|---|---|
| phosphat buffer (% by weight) | 99 | 95 | 90 | 85 | 80 |
| inositol (% by weight) | 1 | 0 | 0 | 10 | 15 |
| sorbitol (% by weight) | 0 | 5 | 0 | 5 | 0 |
| sucrose (% by weight) | 0 | 0 | 10 | 0 | 5 |
| osmotic regulator and concentration (mol/L) | sodium chloride 0.9 | potassium chloride 0.5 | sodium chloride 0.9 | potassium chloride 0.5 | sodium chloride 0.9 |
| osmotic pressure (mOsm/kg) | 200 | 300 | 400 | 450 | 500 |
| virus titre (pfu/mL) | $10^6$ | $10^7$ | $10^8$ | $10^9$ | $10^{10}$ |

The recombinant adenovirus pAd-GFP-G261 or pAd-GFP-G262 from Example 2 was respectively injected q.d. at a dosage of $10^{10}$ pfu/Kg body weight through vena caudalis for 3 successive days. Each formulation was injected into two rats.

(2) Method for Assaying Blood Glucose.

Assay of blood glucose was performed on 0.5 mL of the blood sample collected from rat angular oculi vein, using blood glucose monitor HEA-214 from OMRON according to the manufacturer's instruction.

(3) Results for Determination of Blood Glucose in Rats.

The animals injected with the recombinant virus vector expressing the wild-type glucokinase (G261) were numbered 1, 2, 3, 4, 5, 6, 7, 8, 9, and 10. The animals injected with the recombinant virus vector expressing the mutant glucokinase (G262) were numbered 11, 12, 13, 14, 15, 16, 17, 18, 19, and 20. Blank blood samples were collected from all rats and assayed for the blood glucose level prior to injection. The post-injection blood samples were collected 8 times at various stages and assayed for the blood glucose level. Time points for sampling and the results determined were shown in Tables 4 and 5.

TABLE 4

Descriptive chart for (G261) blood glucose (GLU mmol/L)

| | | 2008-12-17 prior to injection | 2008-12-27 post injection | 2008-12-29 post injection | 2009-1-8 post injection | 2009-1-14 post injection | 2009-1-20 post injection | 2009-1-27 post injection | 2009-2-5 post injection | 2009-2-11 post injection |
|---|---|---|---|---|---|---|---|---|---|---|
| G261 | 1 | 17.4 | 11.2 | 13.8 | 15.2 | 16.1 | 17.1 | 17.5 | 17.6 | 17.5 |
| | 2 | 16.9 | 10.8 | 14 | 14.9 | 15.5 | 16.5 | 11.8 | 16.8 | 16.7 |
| | 3 | 14.2 | 10.6 | 11.8 | 15.2 | 15.1 | 14.1 | 14 | 14.1 | 14.3 |
| | 4 | 17.5 | 13.4 | 13.2 | 14.2 | 15.3 | 16.9 | 17.4 | 17.3 | 17.2 |
| | 5 | 17.8 | 13.2 | 13.8 | 15.1 | 15.2 | 17.1 | 17.6 | 17.4 | 17.6 |
| | 6 | 18.5 | 12.1 | 13.7 | 14.9 | 15.2 | 17.9 | 18.1 | 18.3 | 18.3 |
| | 7 | 19.5 | 11.8 | 12.9 | 14.1 | 15.8 | 18.1 | 18.8 | 19.6 | 19.1 |
| | 8 | 18.3 | 11.5 | 13.2 | 15.1 | 14.9 | 18.2 | 18.1 | 18.2 | 18.4 |
| | 9 | 16.8 | 10.8 | 12.9 | 13.2 | 14.2 | 16.1 | 16.5 | 16.5 | 16.9 |
| | 10 | 18.6 | 11.2 | 12.6 | 14.3 | 15.2 | 16.8 | 18.3 | 18.4 | 18.3 |
| mean | | 17.55 | 11.66 | 13.19 | 14.62 | 15.25 | 16.88 | 16.74 | 17.42 | 17.43 |

TABLE 5

Descriptive chart for (G262) blood glucose (GLU mmol/L)

| | | 2008-12-17 prior to injection | 2008-12-27 post injection | 2008-12-29 post injection | 2009-1-8 post injection | 2009-1-14 post injection | 2009-1-20 post injection | 2009-1-27 post injection | 2009-2-5 post injection | 2009-2-11 post injection |
|---|---|---|---|---|---|---|---|---|---|---|
| G262 | 11 | 13.4 | 6.9 | 7.7 | 8.5 | 7.2 | 7.6 | 7.0 | 6.8 | 6.9 |
| | 12 | 19.7 | 12.5 | 11.0 | 6.8 | 8.7 | 8.1 | 8.9 | 7.4 | 6.8 |
| | 13 | 19.0 | 7.8 | 8.4 | 8.3 | 8.5 | 8.7 | 7.7 | 7.2 | 9.2 |
| | 14 | 15.7 | 10.4 | 10.0 | 8.1 | 9.8 | 9.9 | 10.2 | 10.3 | 8.8 |
| | 15 | 19.5 | 8.0 | 10.3 | 8.5 | 8.5 | 7.4 | 7.2 | 7.9 | 9.7 |
| | 16 | 14.4 | 6.8 | 8.2 | 12.4 | 1.3 | 9.6 | 8.9 | 8.8 | 8.2 |
| | 17 | 18.4 | 5.8 | 9.8 | 7.9 | 10.8 | 10.2 | 9.9 | 9.7 | 8.9 |
| | 18 | 18.0 | 12.2 | 10.8 | 10.2 | 9.3 | 7.9 | 7.6 | 7.2 | 7.1 |
| | 19 | 13.8 | 8.8 | 8.2 | 7.9 | 8.5 | 8.8 | 8.2 | 7.8 | 6.3 |
| | 20 | 17.8 | 9.9 | 11.2 | 10.1 | 8.5 | 7.7 | 8.4 | 8.8 | 7.5 |
| mean | | 16.97 | 8.91 | 9.56 | 8.87 | 8.11 | 8.59 | 8.4 | 8.19 | 7.94 |

It can be seen from the data recorded in Tables 4 and 5 that the in vivo activity of the human glucokinase mutant of the present disclosure to decrease the blood glucose level and stability thereof are much better than those of the human wild-type glucokinase. The blood glucose level in the rat model of type II diabetes mellitus can be effectively controlled by injecting into the animal body the recombinant adenovirus which comprises the human glucokinase mutant-encoding gene of the present disclosure, thus enabling treatment of diabetes mellitus through effectively increasing insulin secretion.

What is claimed is:

1. A human glucokinase encoding gene, wherein the human glucokinase encoding gene is:
   an isolated nucleotide sequence as shown by the whole of SEQ ID NO: 2; or
   an isolated nucleotide sequence that is identical to the nucleotide sequence shown by the whole of SEQ ID NO: 2 except the open reading frame (ORF) ranging from position 487 to 1884 of the nucleotide sequence shown by the whole of SEQ ID NO: 2, the ORF encoding the same amino acid sequence as that encoded by the ORF of the nucleotide sequence shown by the whole of SEQ ID NO: 2.

2. A recombinant vector comprising a vector and a gene of interest carried thereon, the gene of interest comprising the human glucokinase encoding gene as set forth in claim 1.

3. The recombinant vector according to claim 2, the vector selected from a group consisting of a cloning vector, a eukaryotic expression vector, a prokaryotic expression vector, and a shuttle vector.

4. The recombinant vector according to claim 2, the vector selected from a group consisting of pIRES2-EGFP, pCMVp-NEO.BAN, pEGFT-Actin, and an adenovirus vector.

5. A host comprising a recombinant vector as set forth in claim 2.

6. The host according to claim 5, the host selected from one or more of *Escherichia coli*, 293 cells, min-6 cells, and human islet beta-cells.

* * * * *